United States Patent
Lien

(10) Patent No.: US 10,076,244 B2
(45) Date of Patent: Sep. 18, 2018

(54) PHYSIOLOGICAL MONITORING SYSTEM

(71) Applicant: TAIWAN AULISA MEDICAL DEVICES TECHNOLOGIES, INC., Taipei (TW)

(72) Inventor: Augustine Yen Lien, Taipei (TW)

(73) Assignee: TAIWAN AULISA MEDICAL DEVICES TECHNOLOGIES, INC., Taipei (TW)

( * ) Notice: Subject to any disclaimer, the term of this patent is extended or adjusted under 35 U.S.C. 154(b) by 0 days.

(21) Appl. No.: 15/645,625

(22) Filed: Jul. 10, 2017

(65) Prior Publication Data

US 2017/0303787 A1  Oct. 26, 2017

Related U.S. Application Data

(63) Continuation-in-part of application No. 14/725,165, filed on May 29, 2015, now abandoned.

(51) Int. Cl.
| | |
|---|---|
| *A61B 5/00* | (2006.01) |
| *A61B 5/11* | (2006.01) |
| *G08B 29/18* | (2006.01) |
| *A61B 7/00* | (2006.01) |
| *G06F 19/00* | (2018.01) |
| *G16H 40/63* | (2018.01) |

(Continued)

(52) U.S. Cl.
CPC .......... *A61B 5/0022* (2013.01); *A61B 5/0013* (2013.01); *A61B 5/0077* (2013.01); *A61B 5/1128* (2013.01); *A61B 5/742* (2013.01); *A61B 5/746* (2013.01); *A61B 7/00* (2013.01); *G06F 19/00* (2013.01); *G08B 29/185* (2013.01); *G16H 40/63* (2018.01); *G16H 40/67* (2018.01); *A61B 5/01* (2013.01); *A61B 5/11* (2013.01); *A61B 2560/0242* (2013.01); *A61B 2560/0431* (2013.01); *A61B 2562/0204* (2013.01); *A61B 2562/029* (2013.01); *A61B 2562/0257* (2013.01); *A61B 2562/0271* (2013.01)

(58) Field of Classification Search
None
See application file for complete search history.

(56) References Cited

U.S. PATENT DOCUMENTS

| | | | |
|---|---|---|---|
| 9,019,099 B2 * | 4/2015 | Fox | A61B 5/0022 340/539.12 |
| 2009/0112072 A1 * | 4/2009 | Banet | A61B 5/0205 600/301 |

* cited by examiner

*Primary Examiner* — Leon-Viet Nguyen
(74) *Attorney, Agent, or Firm* — Ming Chow; Sinorica, LLC

(57) ABSTRACT

A physiological monitoring system includes a near-end portable monitoring module for generating first sensed data, capturing a user's first image, an image sensing module for synchronizing the first sensed data and the first image to form first combination data, and searching and connecting the corresponding near-end portable monitoring module to receive the first sensed data and display the near-end information display module corresponding to the screen of the first combination data, when the first sensed data includes a warning signal, the first combination data is transmitted and stored in the Internet by the second communication unit within a time period from a first time before the warning signal is issued to a second time for releasing the warning signal, and the first combination data within the time period from the first time to the second time is transmitted to the near-end information display module to display the first combination data.

12 Claims, 8 Drawing Sheets

(51) Int. Cl.
*G16H 40/67* (2018.01)
*A61B 5/01* (2006.01)

PHYSIOLOGICAL MONITORING SYSTEM

FIELD OF THE INVENTION

The present invention relates to the field of physiological monitoring technology, in particular to a physiological monitoring system for monitoring the physiological status and/or image of a user wearing a portable monitoring module.

BACKGROUND OF THE INVENTION

In general, a conventional medical healthcare system allows patients to call a doctor or medical professional by an active method such as ringing an alarm bell. However, such arrangement is very inconvenient to the patients. In some special situations, the patients may be unable to call actively. The same situation may occur in a home care environment. Although a sensing device may be installed to obtain the condition and situation of a care receiver, yet only data are transmitted, and there are still a lot of inconveniences.

In addition, no automatic or manual pairing mechanism is established between the conventional sensing device and monitoring device connected through the Internet, and thus there is an issue of having errors or disorders in the transmission of information between the conventional sensing device and monitoring device via the Internet.

In view of the aforementioned problems, the present invention provides a physiological monitoring system to improve the conventional physiological information and image capturing device.

SUMMARY OF THE INVENTION

It is a first objective of the present invention to provide a physiological status monitoring system comprising a near-end portable monitoring module and an image sensing module, so that after a user wears the near-end portable monitoring module, the image sensing module and/or the near-end information display module may receive the sensed data transmitted from the near-end portable monitoring module to monitor the user's physiological status and/or image. In addition, the near-end information display module may be used for searching and connecting the corresponding near-end portable monitoring module.

A second objective of the present invention is to monitor another user's physiological status and/or image by another far-end portable monitoring module based on the aforementioned monitoring system, in addition to the near-end portable monitoring module, so as to achieve the effect of monitoring the physiological status and/or image of one or more users.

A third objective of the present invention is to provide a monitoring system comprising a near-end information display module and/or a far-end information display module, for displaying the user's physiological status and/or image, so that the user or any non-user (such as a therapist, a nurse, a caregiver) can monitor the user by the information display modules.

A fourth objective of the present invention is to provide the aforementioned monitoring system further comprising an alarm unit, such that when there is an abnormal image and/or physiological status, the alarm unit warns the user or other non-users.

A fifth objective of the present invention is to provide the aforementioned monitoring system, wherein the near-end portable monitoring module, the image sensing module and the near-end information display module may have unidirectional or bisectional data transmission with one another through communication units in compliance with a cable communication or wireless communication specification, and stable and convenient installations may be conducted in different environments.

To achieve the aforementioned and other objectives, the present invention provides a monitoring system for monitoring at least one of a user's physiological status and first image, comprising: a near-end portable monitoring module, an image sensing module and a near-end information display module. The near-end portable monitoring module comprises a first communication unit and a first sensing unit. The near-end portable monitoring module is provided for the user to wear. The first sensing unit senses the user's physiological status to generate first sensed data. The first communication unit transmits the sensed data. The image sensing module comprises a second communication unit and an image capturing unit. The second communication unit receives the first sensed data, and the image capturing unit selectively captures a first image of the user. Wherein, the image capturing unit tracks the user by the near-end portable monitoring module to obtain the first image. The near-end information display module comprises a third communication unit and a first display unit. The third communication unit receives the sensed data and displays a frame corresponds to the first sensed data through the first display unit.

A sixth objective of the present invention is to provide a monitoring system capable of storing a physiological status and an image occurred within a certain period of time before the warning signal is issued up to the warning signal release time and provided for the near-end information display module to backtrack and browse the warning signal history at that time and now to confirm the actual situation of the warning signal.

A seventh objective of the present invention is to synchronize the monitored user's physiological signal and image in the image sensing module by the aforementioned monitoring system to prevent disorders and errors occurred during the transmission of information.

To achieve the aforementioned and other objectives, the present invention provides a monitoring system for monitoring a user's physiological status, or a physiological status and a first image, comprising: a near-end portable monitoring module, an image sensing module, and a near-end information display module. The near-end portable monitoring module comprises a first communication unit and a first sensing unit. The near-end portable monitoring module is provided for the user to wear. The first sensing unit senses the user's physiological status to generate a first sensed data. The first communication unit transmits the sensed data. The image sensing module comprises a second communication unit and an image capturing unit. The second communication unit receives the first sensed data, and the image capturing unit selectively captures the user's first image, wherein the image capturing unit uses the near-end portable monitoring module to track the user to capture the first image, and the image sensing module synchronizes the first sensed data and the first image to form a first combination data. The near-end information display module comprises a third communication unit and a first display unit. The near-end information display module uses the third communication unit to connect to the to search and connect to the corresponding near-end portable monitoring module to receive the first sensed data and display the first sensed data from a screen of the first display unit to where the first combination data is transmitted from the image sensing module, when the first sensed data includes a warning signal, the first combination data is transmitted and stored in the Internet by the second communication unit within a time period from a first time before the warning signal is issued to a second time for releasing the warning signal, and the first combination data within the time period from the first time to the second time is transmitted to the near-end information display module to display the first combination data.

Compared with the prior art, the present invention provides a monitoring system for monitoring one or more users who wear a portable monitoring module, and the image sensing module is provided for receiving the aforementioned user's physiological status and selectively capturing the user's image, and the display module is provided for displaying the related physiological status and image. In addition, the present invention may also adopt the automatic pairing control to avoid displaying the wrong user information and the invention also has the effects of storing correct sensed data of the user within the time period before and after an abnormal situation occurs, and synchronizing the sensed data with the corresponding image
so that the present invention can be applied extensively in different fields such as the fields of security surveillance, pet monitoring, home care, and medical institutes.

DESCRIPTION OF THE PREFERRED EMBODIMENTS

The aforementioned and other objects, characteristics and advantages of the present invention will become apparent with the detailed description of the preferred embodiments and the illustration of related drawings as follows.

Figure 1:
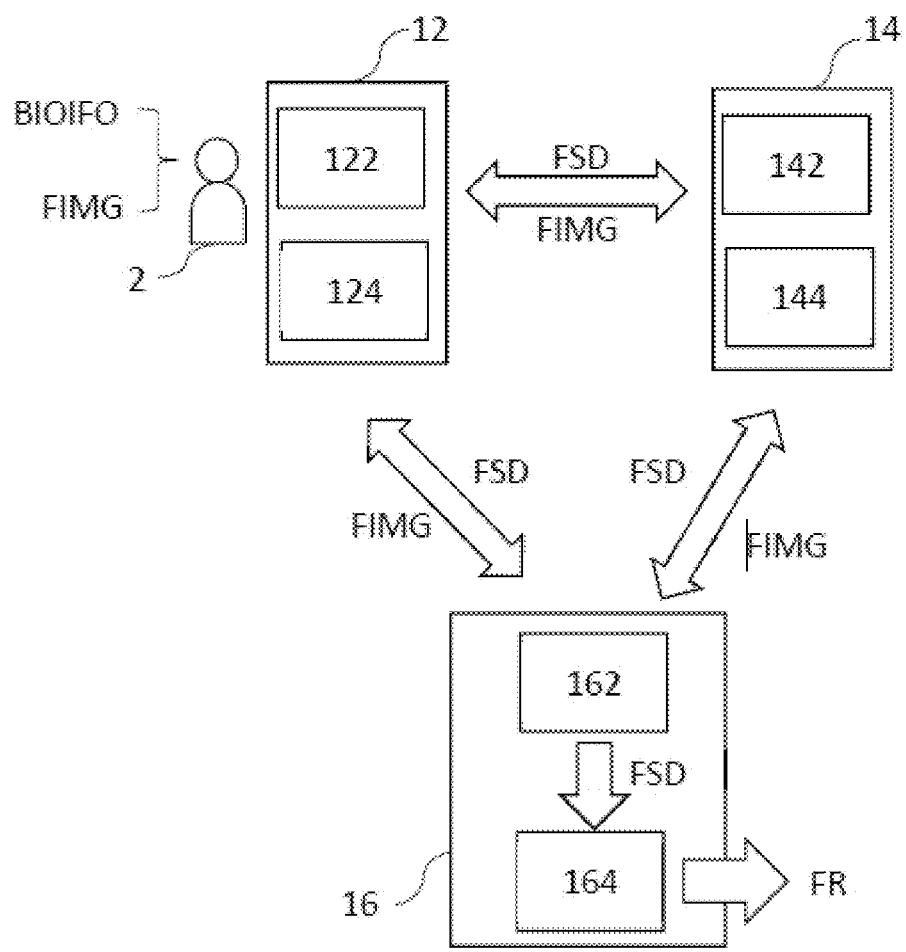
FIG. 1 is a schematic block diagram of a physiological monitoring system in accordance with a first preferred embodiment of the present invention.

With reference to FIG. 1 for a schematic block diagram of a physiological monitoring system in accordance with the first preferred embodiment of the present invention, the physiological monitoring system 10 comprises a near-end portable monitoring module 12, an image sensing module 14 and a near-end information display module 16, and the physiological monitoring system 10 is provided for monitoring a physiological status BIOIFO or a physiological status BIOIFO and a first image FIMG.

The near-end portable monitoring module 12 further comprises a first communication unit 122 and a first sensing unit 124. The near-end portable monitoring module 12 is provided for the user 2 to wear and for sensing the physiological status BIOIFO of the user 2 to generate first sensed data FSD. For example, the first sensing unit 122 is provided for sensing temperature, audio frequency, sound, humidity, brightness, movement, vital signs, physiological signal and distance. The first communication unit 122 is provided for transmitting the first sensed data FSD. For example, the near-end portable monitoring module 12 may be in form of a watch or a piece of jewelry. Wherein, the first communication unit 122 complies with a wireless communication specification and/or a cable communication specification. For the first communication unit 122 complying with the wireless communication specification, the wireless communication specification includes a short-range communication protocol and a long-range communication protocol. The short-range communication protocol may be a near field communication protocol, a Bluetooth communication protocol, a ZigBee communication protocol, a digital enhanced cordless telecommunications protocol or a wireless universal serial bus communication protocol; and the long-range communication protocol may be a wireless fidelity (Wi-Fi) communication protocol, a municipal wireless communication protocol, a general packet radio service communication protocol, a wireless broad band communication protocol, a worldwide inter operability for microwave access communication protocol, a time division duplexing communication protocol, a high speed packet access communication protocol, a high speed down link packet access communication protocol, or a long term evolution communication protocol.

The image sensing module 14 comprises a second communication unit 142 and an image capturing unit 144. The second communication unit 142 receives the first sensed data FSD, wherein the second communication unit 142 is the same as the first communication unit 122 as described above. The image capturing unit 144 selectively captures a first image FIMG of the user 2. For example, the image capturing unit 144 is a charge coupled device (CCD) or a complimentary metal oxide semiconductor (CMOS) component, and the resolution is a standard definition (SD) resolution or a high density (HD) resolution. Wherein, the image capturing unit 144 tracks the user 2 by the near-end portable monitoring module 12 to obtain the first image FIMG.

The near-end information display module 16 comprises a third communication unit 162 and a first display unit 164. The third communication unit 162 receives the first sensed data FSD and the synchronized first image FMG thereof. The third communication unit 162 receives the first sensed data FSD. Wherein, the third communication unit 162 is the same as the first communication unit 122 as described above. In addition, the first display unit 164 displays a frame FR corresponds to the first sensed data FSD and the synchronized first image FIMG thereof. For example, at least one of the physiological status and image is displayed in the frame FR and provided for the user 2 or the non-user to monitor the physiological status and/or image.

It is noteworthy that a unidirectional or bisectional transmission of data may be conducted among the near-end portable monitoring module 12, the image sensing module 14 and the near-end information display module 16, and the transmission of commands/control signals in another transmission direction can be conducted.

Figure 2:
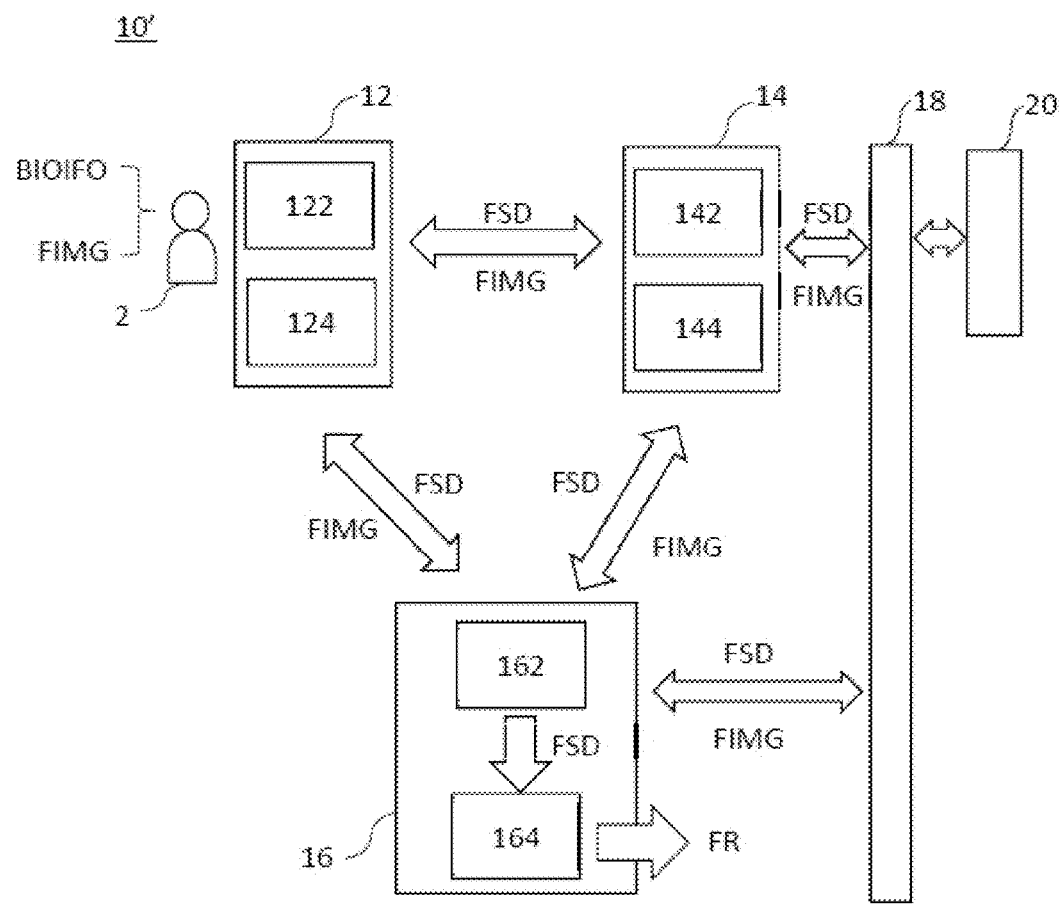
FIG. 2 is a schematic block diagram of a physiological monitoring system in accordance with a second preferred embodiment of the present invention.

With reference to FIG. 2 for the schematic block diagram of a physiological monitoring system in accordance with the second preferred embodiment of the present invention, the physiological monitoring system 10' further comprises a network communication unit 18 in addition to the near-end portable monitoring module 12, the image sensing module 14 and the near-end information display module 16 described in the first preferred embodiment.

The network communication unit 18 is connected to the Internet 20. The network communication unit 18 complies with a communication specification, and the communication specification also complies with at least one of the aforementioned wireless communication specification and cable communication specification. The network communication unit 18 may transmit the first sensed data FSD among the near-end portable monitoring module 12, the image sensing module 14 and the near-end information display module 16 via the Internet 20. The Internet 20 may be a network having the network computing and/or network control ability such as the ability of cloud computing, distributed system, and server.

Figure 3:
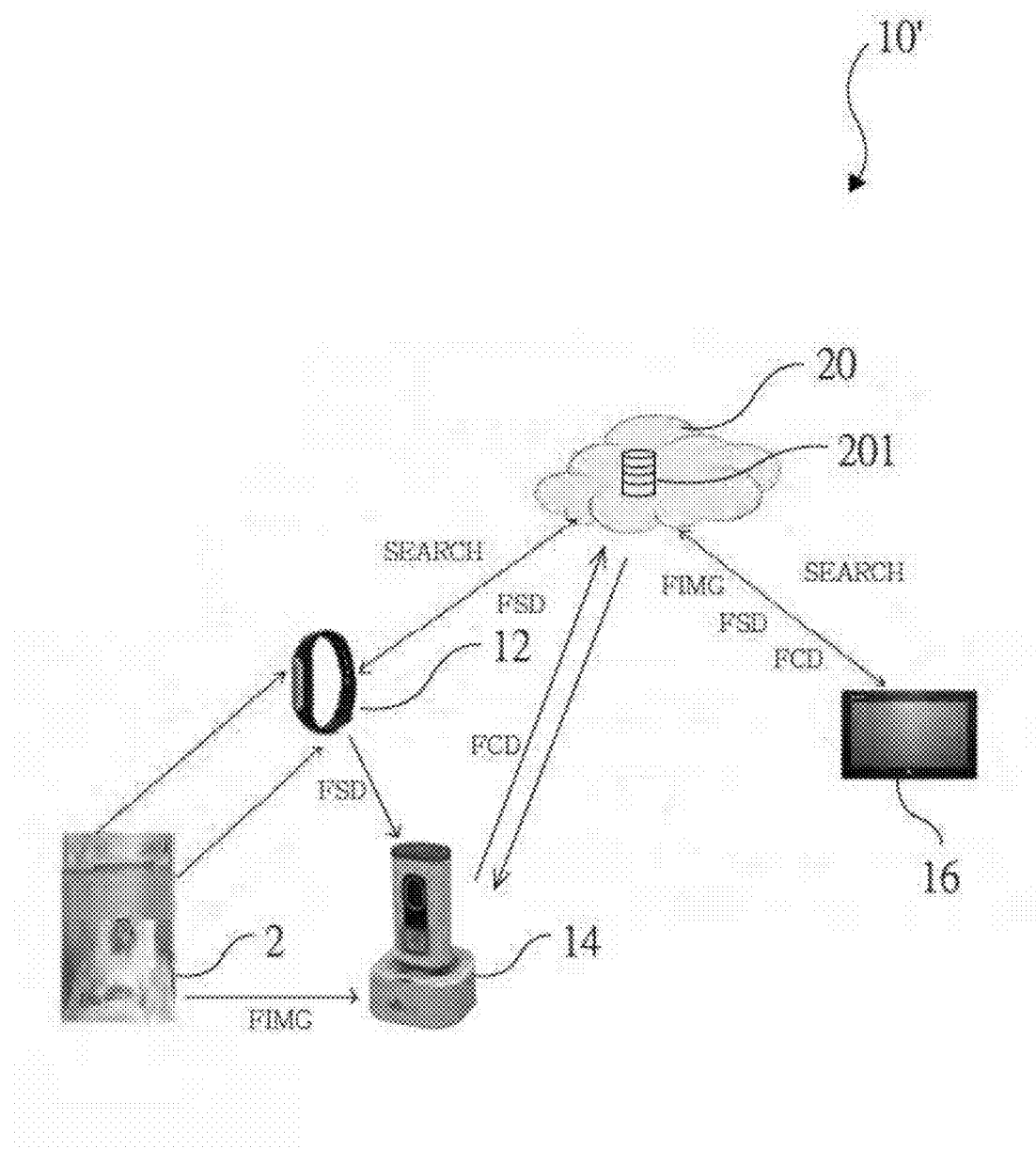
FIG. 3 is a schematic view of a physiological monitoring system being paired and at least storing sensed data by the Internet in accordance with the second preferred embodiment of the present invention.

With reference to FIG. 3 for the schematic view showing the near-end information display module 16 of physiological monitoring system 10' in accordance with the second preferred embodiment of the present invention searches and connects the corresponding near-end portable monitoring module 12, and the physiological monitoring system 10' at least stores the sensed data, the near-end information display module 16 uses the third communication unit 162 to search and connect the corresponding near-end portable monitoring module 12 to receive the first sensed data FSD and display a screen corresponding to the first sensed data FSD on the first display unit 164. Specifically, the near-end information display module 16 may include a memory unit or a storage unit such as a flash memory or a hard disk, and the near-end information display module 16 uses the third communication unit 162 searches and connects the corresponding near-end portable monitoring module 12 to receive the first sensed data FSD, and the method for the physiological monitoring system 10' to store the sensed data firstly stores the address of the near-end portable monitoring module 12 into the memory unit or storage unit as shown in Step S401 of FIG. 4.

A two-dimensional bar code (such as the QR code) may be used to scan the media access control address (MAC address) of the near-end portable monitoring module 12 which may be stored in the memory unit or storage unit of the near-end information display module 16, but the method of storing the MAC address of the present invention is not limited to the aforementioned arrangement only.

Figure 4:
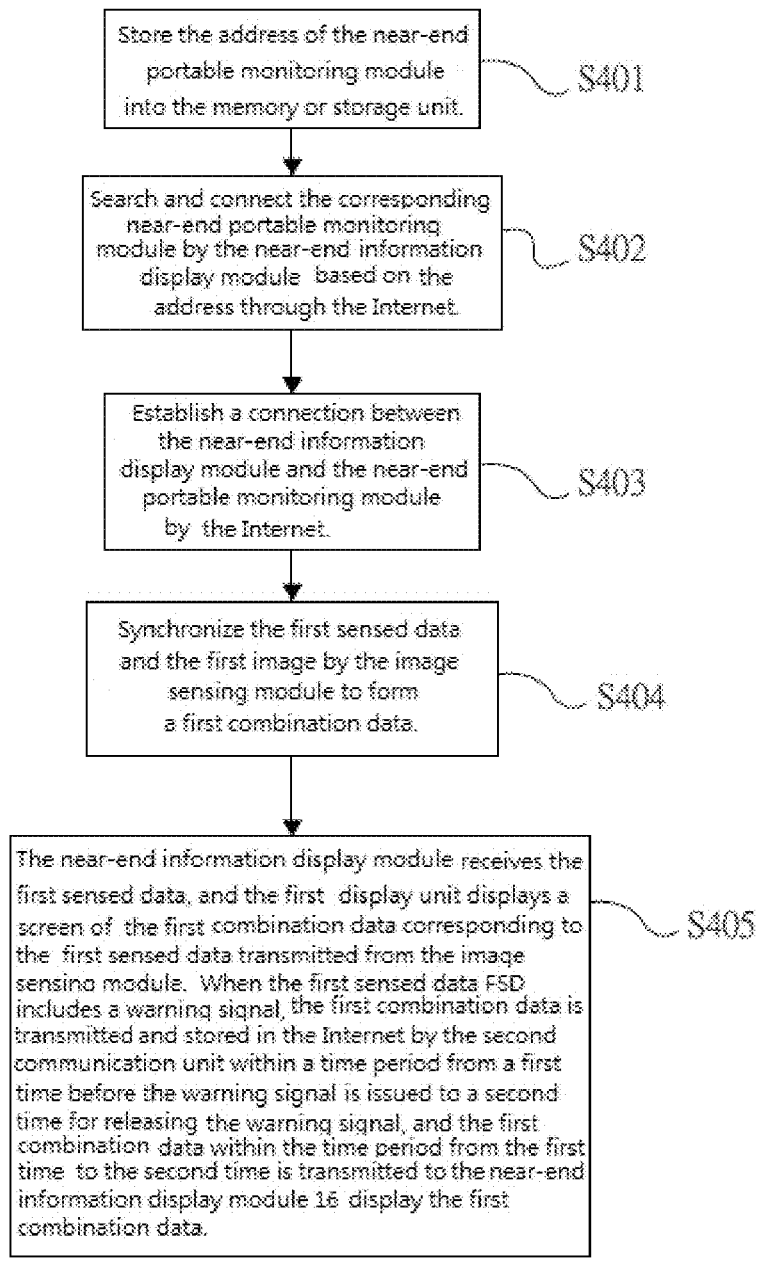
FIG. 4 is a flow chart of the physiological monitoring system being paired and storing sense data by the Internet in accordance with the second preferred embodiment of the present invention.

In Step S402 as shown in FIG. 4, the near-end information display module 16 searches and connects the corresponding near-end portable monitoring module 12 based on the address through the Internet 20. The near-end information display module 16 and the near-end portable monitoring module 12 may be a mobile phone, a tablet PC, or a notebook computer with the communication function. Specifically, the near-end information display module 16 may use the MAC address of the near-end portable monitoring module 12 stored in the memory unit or storage unit automatically or manually through the Internet 20 to search the near-end portable monitoring module 12 corresponding to the MAC address. Of course, the near-end information display module 16 may use the unique identification code assigned to the near-end portable monitoring module 12 and stored in the memory unit or storage unit to connect with near-end portable monitoring module 12.

In Step S403 as shown in FIG. 4, the Internet 20 establishes a connection between the near-end information display module 16 and the near-end portable monitoring module 12. Specifically, a receiver/transponder may search a previously paired near-end portable monitoring module 12 by cloud computing, and the binding between the near-end portable monitoring module 12 and the near-end information display module 16 may be established through cloud computing.

When the portable monitoring module 12 and the near-end information display module 16 are bounded and paired by cloud computing, the receiver/transponder of the cloud computing will establish a P2P channel with the near-end information display module 16 or a unique communication channel between the paired near-end information display module 16 and portable monitoring module 12, so that the near-end information display module 16 and the portable monitoring module 12 may communicate with each other, and related physiological information may be display from the near-end information display module 16.

In Step S404 as shown in FIG. 4, the image sensing module 14 synchronizes the first sensed data FSD and the first image FIMG to form a first combination data FCD. The first combination data FCD may be transmitted to the second communication unit 142. It is noteworthy that the first combination data FCD may be the first sensed data FSD, the first image FIMG, or a combination of the first sensed data FSD and the first image FIMG.

In Step S405 as shown in FIG. 4, the near-end information display module 16 receives the first sensed data FSD, and the first display unit 164 displays a screen of the first combination data FCD corresponding to the first sensed data FSD transmitted from the image sensing module 14. When the first sensed data FSD includes a warning signal, the first combination data is transmitted and stored in the Internet by the second communication unit 142 within a time period from a first time before the warning signal is issued to a second time for releasing the warning signal, and the first combination data within the time period from the first time to the second time is transmitted to the near-end information display module 16 to display the first combination data.

In addition, the near-end information display module 16 shows the connecting status between the near-end information display module 16 and the Internet 20, and the connecting status between the near-end portable monitoring module 12 and the Internet 20. For example, when the near-end information display module 16 and the Internet 20 are connected or disconnected, the third communication unit 162 of the near-end information display module 16 makes the near-end information display module 16 to show the connection or disconnection between the near-end information display module 16 and the Internet 20. When the near-end information display module 16 and the Internet 20 are connected, the Internet 20 may make the near-end information display module 16 to show the connection between near-end information display module 16 and the Internet 20. When the near-end portable monitoring module 12 and the Internet 20 are disconnected, the Internet 20 makes the near-end information display module 16 to show the near-end portable monitoring module 12 and the Internet 20 are connected or disconnected.

In FIG. 3, the Internet 20 includes an Internet storage unit 201 for storing the first combination data FSD within the time period from the first time to the second time. Specifically, the receiver/transponder of cloud computing not just transmits data only, but also combines the first sensed data FSD with the first image FIMG and sound and achieves a synchronous effect. In addition, all information collected within the time period before a physiological status at issue occurs to the time when the problem is still unsolved will be transmitted and stored into the cloud computing for future tracking and inquiry.

Figure 5:
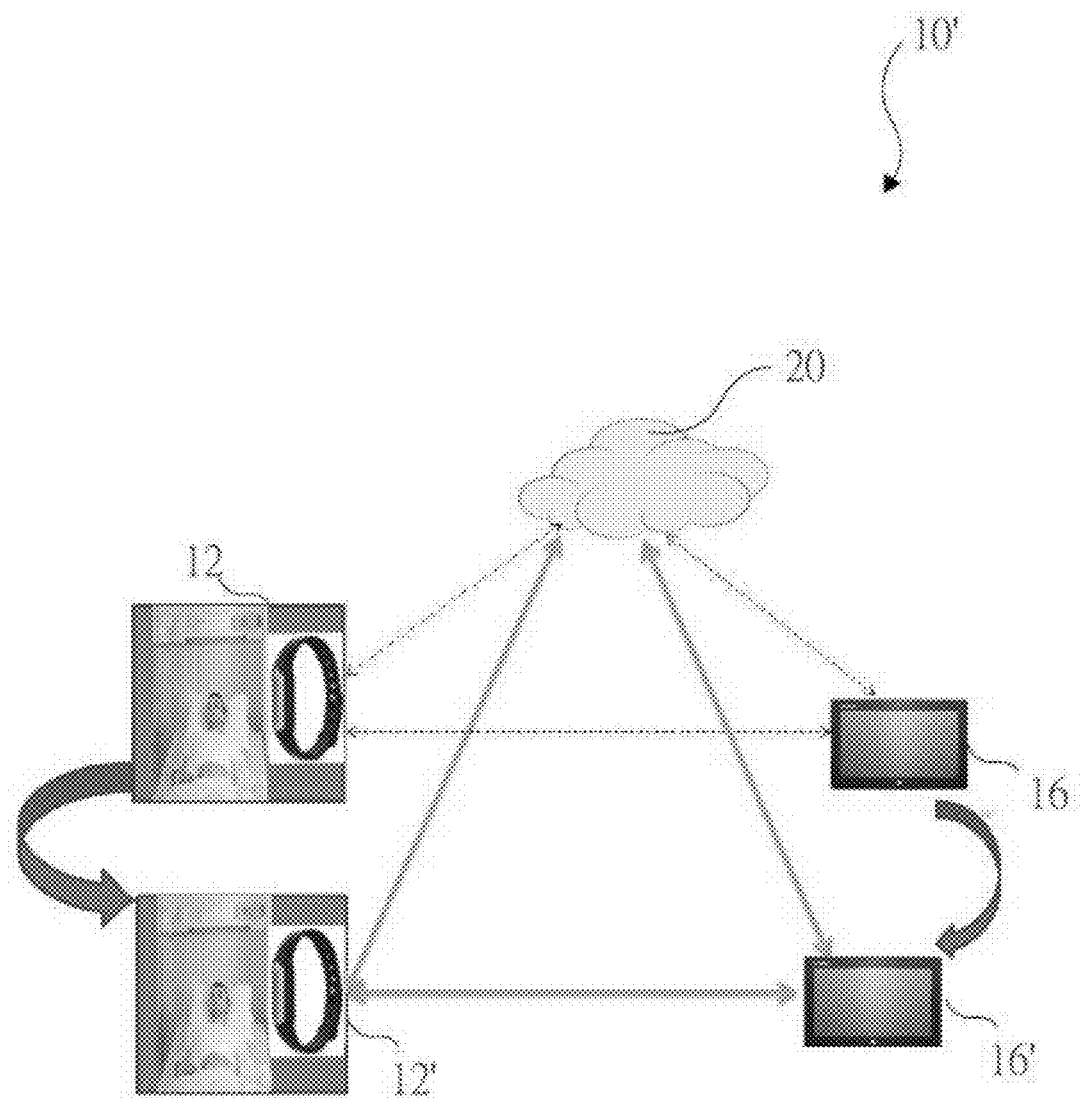
FIG. 5 is a schematic view of a physiological monitoring system being paired by the Internet and automatically maintaining a search with a self-organizing ability in accordance with the second preferred embodiment of the present invention.

In FIG. 5, all devices (including the near-end portable monitoring module 12, the near-end information display module 16, etc) may be mobile devices. When the device is moving within a transmission range, the devices automatically maintain a self-organizing search without causing an interrupt of the monitoring process. In FIG. 5, the near-end portable monitoring module 12 worn by the user 2 may be separated from the receiver/transponder of the Internet 20, but at least a normal communication between the near-end portable monitoring module 12 and the receiver/transponder of the Internet 20 can be maintained, and the near-end information display module 16 may be communicated with the receiver/transponder of the Internet 20 normally. While moving, the near-end portable monitoring module 12' and the near-end information display module 16' still can communicate with the receiver/transponder of the Internet 20 normally. In FIG. 5, the near-end information display module 16 and the receiver/transponder are connected to the cloud computing equipment, so that they can be connected to cloud computing as long as their communication distance falls within the range of 3G/4G/5G or future developed long-distance communication protocol. Of course, the wireless mobile communication can be accomplished by satellite.

Figure 6:
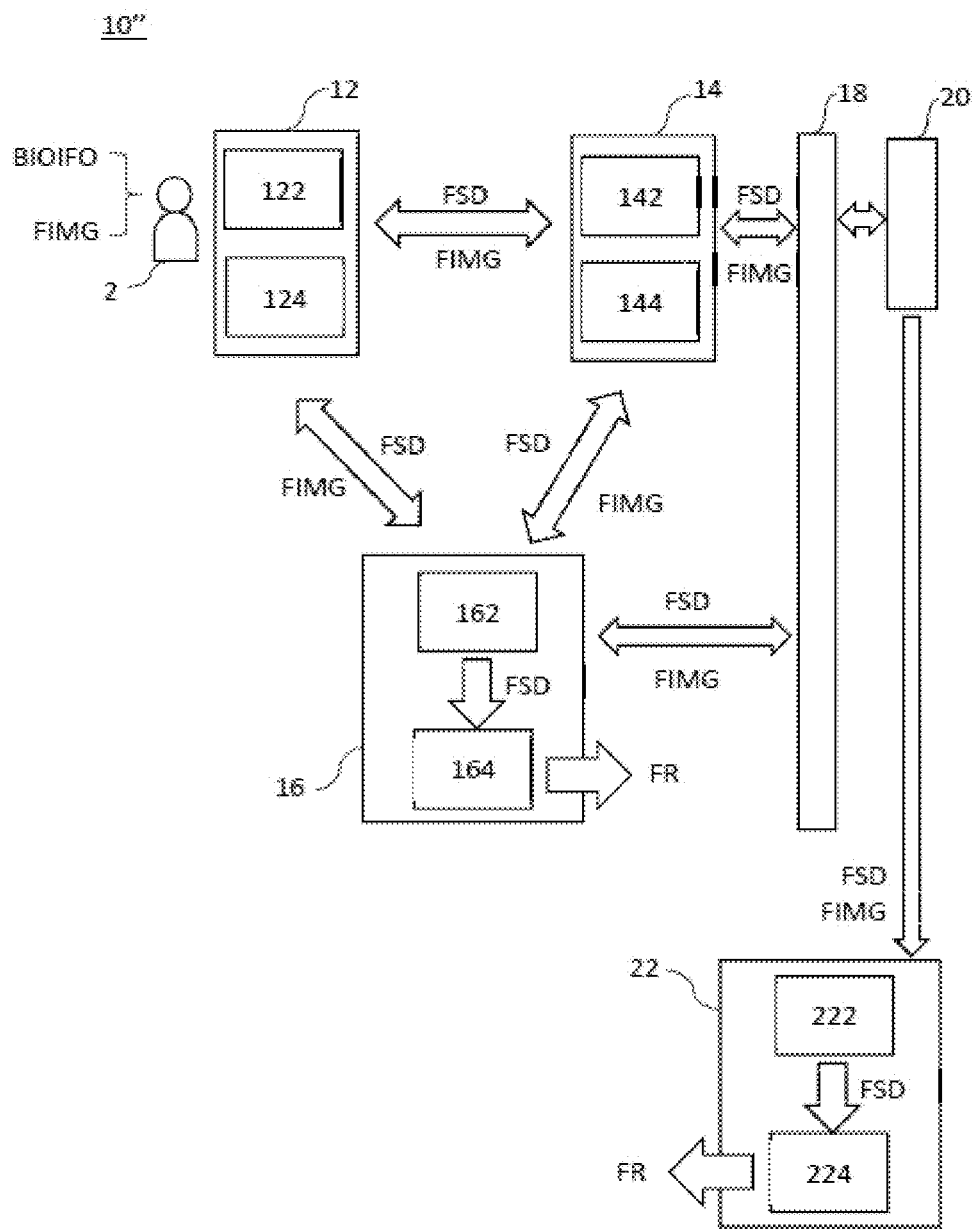
FIG. 6 is a schematic block diagram of a physiological monitoring system in accordance with a third preferred embodiment of the present invention.

With reference to FIG. 6 for the schematic block diagram of a physiological monitoring system in accordance with the third preferred embodiment of the present invention, the physiological monitoring system 10" further comprises a far-end information display module 22 in addition to the near-end portable monitoring module 12, the image sensing module 14, the near-end information display module 16, the network communication unit 18, and the Internet 20 as described in the second preferred embodiment.

The far-end information display module 22 comprises a fourth communication unit 222 and a second display unit 224. The fourth communication unit 222 receives the first sensed data FSD and the synchronized first image FIMG via the Internet 20 and displays the frame FR corresponds to the first sensed data FSD and the synchronized first image FIMG on the second display unit 224. Wherein, the fourth communication unit 222 also complies with at least one of the aforementioned wireless communication specification and cable communication specification.

The far-end information display module 22 is connected to the Internet 20 directly or through the network communication unit 18 to receive the first sensed data FSD and the synchronized first image FIMG.

Figure 7:
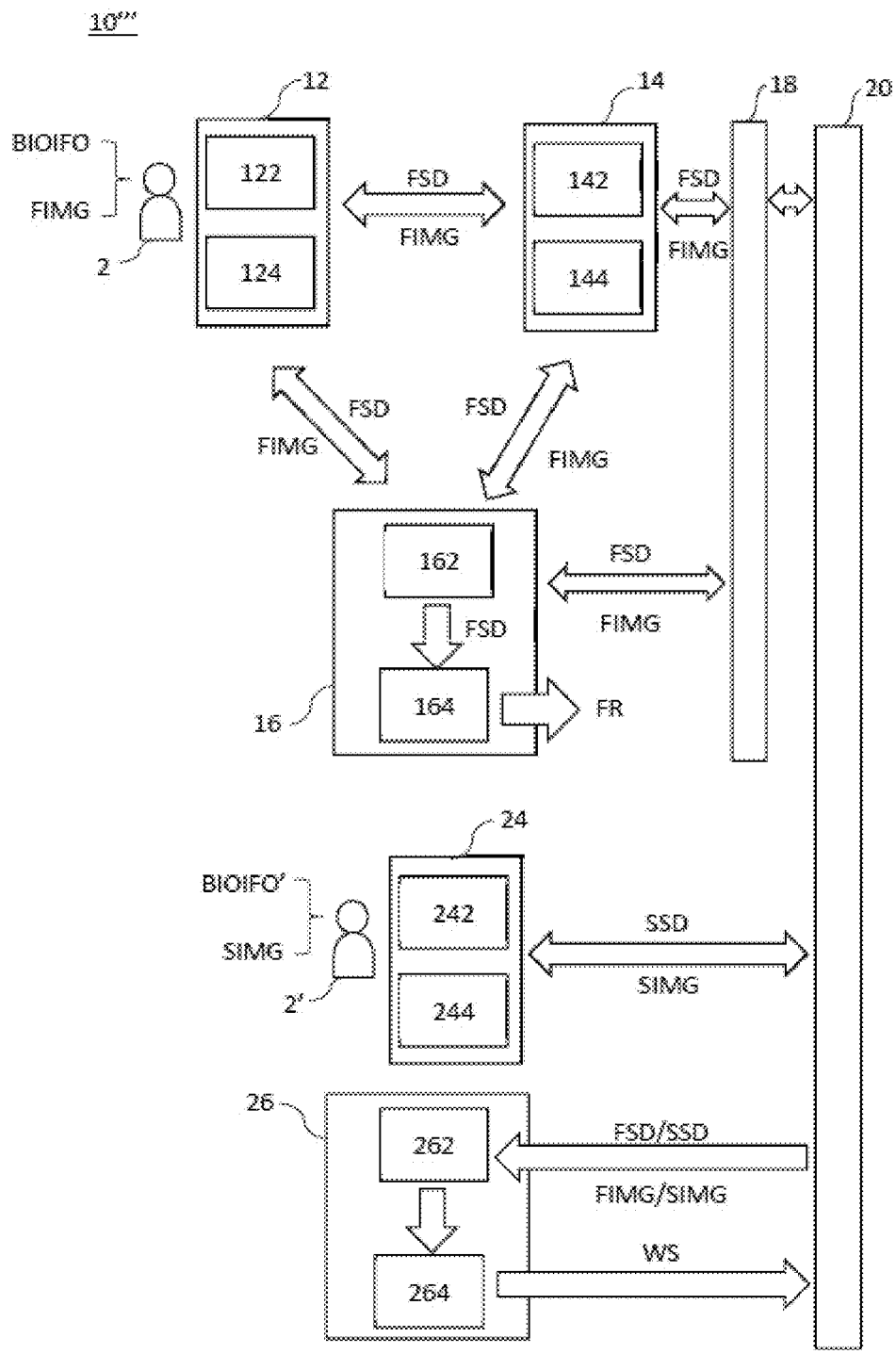
FIG. 7 is a schematic block diagram of a physiological monitoring system in accordance with a fourth preferred embodiment of the present invention.

With reference to FIG. 7 for the schematic block diagram of a physiological monitoring system in accordance with the fourth preferred embodiment of the present invention, the physiological monitoring system 10''' further comprises a far-end portable monitoring module 24 and an alarm unit 26 in addition to the near-end portable monitoring module 12, the image sensing module 14, the near-end information display module 16, the network communication unit 18, and the Internet 20 as described in the second preferred embodiment. The physiological monitoring system 10''' is provided for monitoring at least one of the physiological status BIOIFO and the first image FIMG of a user 2 as well as monitoring at least one of the physiological status BIOIFO' and the second image SIMG of another user 2'.

The far-end portable monitoring module 24 comprises a fifth communication unit 242 and a second sensing unit 244. The far-end portable monitoring module 24 is provided for the other user 2' to wear. The second sensing unit 244 senses the physiological status BIOIFO' and/or the second image SIMG of the other user 2' to generate second sensed data SSD. The fifth communication unit 242 transmits at least one of the second sensed data SSD, or the second sensed data SSD and the second image SIMG and the second image SIMG to the Internet 20. Wherein, the second sensing unit 244 is provided for sensing at least one selected from the group consisting of temperature, audio frequency, sound, humidity, brightness, movement, vital sign, physiological signal and distance.

The alarm unit 26 comprises a sixth communication unit 262 and a first processing unit 264. The sixth communication unit 262 receives the second sensed data SSD, and the first processing unit 264 selectively generates a warning signal WS according to the second sensed data SSD. The warning signal WS is provided for warning an abnormal situation of the user 2 and the user 2'.

When the Internet 20 further includes the Internet storage unit 201 for at least storing a warning signal WS, the Internet storage unit 201 also stores the first sensed data FSD and the synchronized first image FMG thereof within the time period before and after the warning signal WS is issued.

When the Internet 20 further includes the Internet storage unit 201, the near-end information display module 16 displays the history track of the physiological status of a user 2 and/or a user 2'. Since the Internet 20 has the device pairing function, therefore errors or disorders of transmitting the information with regard to the history track of the physiological status can be avoided.

Figure 8:
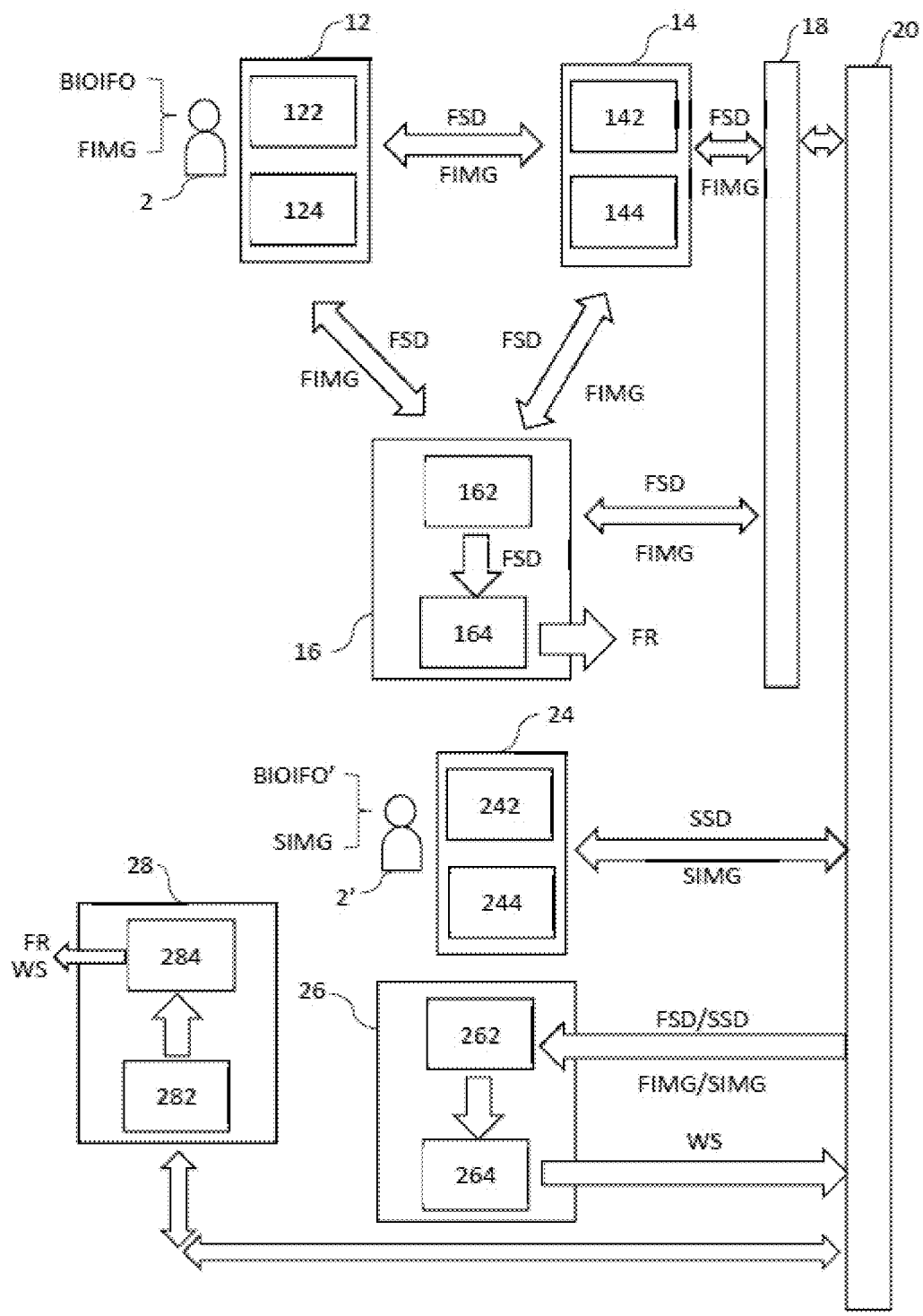
FIG. 8 is a schematic block diagram of a physiological monitoring system in accordance with a fifth preferred embodiment of the present invention.

With reference to FIG. 8 for the schematic block diagram of a physiological monitoring system in accordance with the fifth preferred embodiment of the present invention, the physiological monitoring system 10'''' further comprises a servo host 28 in addition to the near-end portable monitoring module 12, the image sensing module 14, the near-end information display module 16, the network communication unit 18, the Internet 20, the far-end portable monitoring module 24 and the alarm unit 26 as described in the fourth preferred embodiment.

The servo host 28 comprises a seventh communication unit 282 and a second host unit 284. The seventh communication unit 282 receives at least one of the first sensed data FSD, the first image FIMG, the second sensed data SSD and the second image SIMG, and the second host unit 284 generates at least one frame FR according to the first image FIMG and the second image SIMG. In addition, the second host unit 284 generates a warning signal WS according to at least one of the first sensed data FSD and the second sensed data SSD.

It is noteworthy that the near-end information display module 16 of the physiological monitoring system 10' in accordance with the second preferred embodiment of the present invention searches and connects the corresponding near-end portable monitoring module 12 and the method used for storing the sensed data by the physiological monitoring system 10' may be applied to the third to fifth preferred embodiment of the present invention.

While the invention has been described by means of specific embodiments, numerous modifications and variations could be made thereto by those skilled in the art without departing from the scope and spirit of the invention set forth in the claims.

What is claimed is:

1. A physiological monitoring system, for monitoring a user's physiological status, or the physiological status and a first image, comprising:
a near-end portable monitoring module, having a first communication unit and a first sensing unit, and provided for the user to wear, and the first sensing unit sensing the physiological status of the user to generate first sensed data, and the first communication unit transmitting the sensed data;
an image sensing module, having a second communication unit and an image capturing unit, and the second communication unit receiving the first sensed data, and the image capturing unit capturing the first image of the user, and the image capturing unit tracking the user to obtain the first image by the near-end portable monitoring module, wherein the image sensing module synchronizes the first sensed data and the first image to form first combination data;
a near-end information display module, having a third communication unit and a first display unit, and the near-end information display module using the third communication unit to connect to the Internet to search and connect to the corresponding near-end portable monitoring module to receive the first sensed data and display the first sensed data from a screen of the first display unit to where the first combination data is transmitted from the image sensing module, when the first sensed data includes a warning signal, the first combination data is transmitted to and stored in an Internet storage unit of the Internet by the second communication unit within a time period from a first time before the warning signal is issued to a second time for releasing the warning signal, and the first combination data within the time period from the first time to the second time is transmitted to the near-end information display module to display the first combination data;
a network communication unit for connecting the Internet, and the network communication unit complying with a communication specification, and at least one of the first communication unit, the second communication unit and the third communication unit complying with the communication specification, so that the first sensed data are transmitted among the near-end portable monitoring module, the image sensing module and the near-end information display module via the Internet; and
the near-end information display module at least shows a connecting status between the near-end information display module and the Internet, and a connecting status between and the near-end portable monitoring module and the Internet.

2. The physiological monitoring system as claimed in claim 1, wherein the first sensing unit is provided for sensing at least one selected from the group consisting of temperature, audio frequency, sound, humidity, brightness, movement vital sign, physiological signal, and distance.

3. The physiological monitoring system as claimed in claim 1, wherein the near-end information display module comprises a memory unit or a storage unit, and the near-end information display module searches and connects the corresponding near-end portable monitoring module, and the physiological monitoring system stores the sensed data through a procedure comprising the steps of : 1) storing the address of the near-end portable monitoring module into the memory unit or storage unit; 2) searching and connecting the near-end portable monitoring module by the near-end information display module based on the address through the Internet; 3) establishing a connection between the near-end information display module and the near-end portable monitoring module by the Internet; 4) synchronizing the first sensed data and the first image by the image sensing module to form first combination data; 5) receiving the first sensed data by the near-end information display module, and displaying the first sensed data from a screen of the first display unit to where the first combination data is transmitted from the image sensing module, when the first sensed data includes a warning signal, the first combination data is transmitted to and stored in the Internet storage unit of the Internet by the second communication unit within a time period from a first time before the warning signal is issued to a second time for releasing the warning signal, and the first combination data within the time period from the first time to the second time is transmitted to the near-end information display module to display the first combination data.

4. The physiological monitoring system as claimed in claim 1, further comprising a far-end information display module having a fourth communication unit and a second display unit, and the fourth communication unit receiving the first sensed data via the Internet and displaying the frame corresponsive to the first sensed data on the second display unit, wherein the fourth communication unit complies with the communication specification.

5. The physiological monitoring system as claimed in claim 1, further comprising a far-end portable monitoring module having a fifth communication unit and a second sensing unit, provided for the user to wear, and the second sensing unit sensing at least one of the physiological status and second image of another user to generate second sensed data, and the fifth communication unit transmitting the second sensed data to the Internet.

6. The physiological monitoring system as claimed in claim 5, wherein the second sensing unit is provided for sensing at least one selected from the group consisting of temperature, audio frequency, sound, humidity, brightness, movement, vital sign, physiological signal, and distance.

7. The physiological monitoring system as claimed in claim 5, further comprising an alarm unit having a sixth communication unit and a first processing unit, and the sixth communication unit receiving the second sensed data, and the first processing unit selectively generating a warning signal according to the second sensed data.

8. The physiological monitoring system as claimed in claim 7, wherein the Internet further comprises an Internet storage unit for storing the warning signal.

9. The physiological monitoring system as claimed in claim 5, wherein the Internet further comprises an Internet storage unit, and the near-end information display module displays the history track of another user's physiological status.

10. The physiological monitoring system as claimed in claim 5, further comprising a servo host having a seventh communication unit and a second host unit, and the seventh communication unit receiving at least one of the first sensed data, the first image, the second sensed data and the second image, and the second host unit generating at least one frame according to the first image and the second image, and the second host unit generating a warning signal according to at least one of the first sensed data and the second sensed data.

11. The physiological monitoring system as claimed in claim 1, further comprising an alarm unit having a sixth communication unit and a first processing unit, and the sixth communication unit receiving the first sensed data, and the processing unit selectively generating a warning signal according to the first sensed data.

12. The physiological monitoring system as claimed in claim 1, further comprising a servo host having a seventh communication unit and a second host unit, and the seventh communication unit receiving at least one of the first sensed data and the image, and the second host unit generating a frame according to the image, and the second host unit generating a warning signal according to at least one of the first sensed data and the image.

* * * * *